(12) United States Patent
Hsu et al.

(10) Patent No.: US 7,666,407 B2
(45) Date of Patent: Feb. 23, 2010

(54) LACTOBACILLUS PARACASEI-CONTAINING PRODUCT

(75) Inventors: Ching-Hsiang Hsu, Tainan County (TW); Ya-Hui Chen, Tainan County (TW); Ying-Yu Wang, Tainan County (TW); Ding-Ying Lai, Tainan County (TW); Feng-Ching Hsieh, Tainan County (TW)

(73) Assignee: GenMont Biotech Inc., Shanhua Township (TW)

( * ) Notice: Subject to any disclaimer, the term of this patent is extended or adjusted under 35 U.S.C. 154(b) by 334 days.

(21) Appl. No.: 11/637,711

(22) Filed: Dec. 13, 2006

(65) Prior Publication Data

US 2008/0118444 A1    May 22, 2008

(30) Foreign Application Priority Data

Aug. 9, 2006   (TW) ............... 95129265 A

(51) Int. Cl.
| | |
|---|---|
| A61K 8/66 | (2006.01) |
| A61K 8/96 | (2006.01) |
| A01N 63/00 | (2006.01) |
| C12N 1/00 | (2006.01) |
| C12N 1/12 | (2006.01) |
| C12N 1/20 | (2006.01) |
| A61K 47/00 | (2006.01) |

(52) U.S. Cl. .................... 424/93.45; 424/50; 424/439; 435/243; 435/252.1; 435/252.9; 435/853

(58) Field of Classification Search ........... None
See application file for complete search history.

(56) References Cited

U.S. PATENT DOCUMENTS

| | | | |
|---|---|---|---|
| 6,036,952 A | 3/2000 | Oh | |
| 6,872,565 B2 | 3/2005 | Mollstam et al. | |
| 6,942,849 B2 | 9/2005 | Neeser et al. | |
| 7,375,080 B1 * | 5/2008 | Naidu | 514/6 |

FOREIGN PATENT DOCUMENTS

| | | |
|---|---|---|
| WO | WO-2006/048457 A1 | 5/2006 |
| WO | WO-2006/088923 A2 | 8/2006 |

OTHER PUBLICATIONS

Kanokporn Pangsomboon et. al., "Antibacterial activity of a bacteriocin from *Lactobacillus paracasei* HL32 against *Porphyromonas gingivalis*", Archives of Oral Biology, vol. 51, No. 9, Sep. 1, 2006, pp. 784-793, XP-005609312.

S. Sookkhee et. al., "Lactic acid bacteria from healthy oral cavity of Thai volunteers: inhibition of oral pathogens", Journal of Applied Microbiology, vol. 90, No. 2, Feb. 1, 2001, pp. 172-179, XP-002321894.

* cited by examiner

*Primary Examiner*—David M. Naff
*Assistant Examiner*—Deborah K. Ware
(74) *Attorney, Agent, or Firm*—Birch, Stewart, Kolasch & Birch, LLP

(57) ABSTRACT

A *Lactobacillus paracasei*-containing product used for inhibiting dental diseases caused by bacteria is provided, which comprises a plurality of *Lactobacillus paracasei* for inhibiting the growth of bacteria of dental diseases. Particularly, foods, oral hygiene products or oral treatment medicine containing the *Lactobacillus paracasei* when being administered or applied to a user can inhibit or reduce the number of pathogens of dental caries and periodontal diseases in oral cavity of the user, thereby achieving the efficacy of preventing dental diseases, such as dental caries and periodontal diseases.

13 Claims, 4 Drawing Sheets

| Pathogen / Lactobacillus | Area of S. mutans antimicrobial cycle (cm) | Area of S. Sobrinus antimicrobial cycle (cm) |
|---|---|---|
| LGG | 0.815± 0.035 | 0.705± 0.025 |
| LP | 0.965± 0.015 | 0.990± 0.060 |

| Pathogen / Reacting time | Porphryomonas gingivalis | Prevotella intermedia | Centipeda periodontii | Clinic sample |
|---|---|---|---|---|
| 1 hour | +++ | ++ | +++ | + |
| 2 hour | ++++ | ++ | ++++ | ++ |
| 4 hour | ++++ | ++ | ++++ | ++ |
| 6 hour |  | +++ |  | ++ |
| 12 hour |  | +++ |  | ++ |

+ : the inhibiting ratio of 50 %, ++ : the inhibiting ratio of 60-70 %, +++ : the inhibiting ratio of 80-90 %, ++++ : the inhibiting ratio of 100 %, Blank: no measurement is conducted after a thorough inhibition effect.

Fig. 4A

| Pathogen / Reacting time | Porphryomonas gingivalis | Prevotella intermedia | Centipeda periodontii | Clinic sample |
|---|---|---|---|---|
| 1 hour | ++ | + | ++ | + |
| 2 hour | ++ | + | ++ | + |
| 4 hour | +++ | ++ | +++ | + |
| 6 hour | +++ | ++ | +++ | + |
| 12 hour | +++ | ++ | +++ | ++ |

+: the inhibiting ratio of 50 %, ++ : the inhibiting ratio of 60-70 %, +++ : the inhibiting ratio of 80 %

Fig. 4B

LACTOBACILLUS PARACASEI-CONTAINING PRODUCT

CROSS-REFERENCE TO RELATED APPLICATIONS

This non-provisional application claims priority under 35 U.S.C. §119(a) on patent application Ser. No(s). 095129265 filed in Taiwan, R.O.C. on Aug. 9, 2006, the entire contents of which are hereby incorporated by reference.

BACKGROUND OF THE INVENTION

1. Field of Invention

The present invention relates to a product used in oral cavity, and more particularly, to a *Lactobacillus paracasei*-containing product used for inhibiting dental diseases caused by bacteria.

2. Related Art

A dental caries is one of multi-factorial diseases caused by the following factors, including constituted element of teeth, configuration, position, component of saliva, pH value, secretion, viscosity, anti-bacterial factors, carbohydrate level in diet, fluoride, and microorganisms and their physical properties. Therefore, reducing the number of bacteria in oral cavity may reduce the occurrence of periodontal diseases caused by dental caries and bacteria. Generally, the bacteria affecting the health care of teeth are all in the form of a dental plaque, which is a film-shaped substance adhered on a surface of teeth in the oral cavity, with the appearance being gradually changed from a transparent appearance into a white deposit. The bacteria in the dental plaque include a variety of cocci, bacilli, and leptothrix, wherein the main bacteria of dental plaques that most easily causes dental caries or a periodontal inflammation include *Streptococcus mutans*, *Streptococcus sanguis*, *Actinomyces viscosus*, *Streptococcus sobrinus*, and *Porphyromonas gingivalis*.

Currently, many researching results show that, special probiotics can reduce the occurrence of dental caries, and also decrease the number of the *Streptococcus mutans* of dental caries in oral cavity, which further reduces the formation of dental plaques so as to decrease a seedbed for pathogens of periodontal disease, and thereby preventing gingivitis and bone loss of an inferior alveolar bone caused by the toxin of bacteria, and reducing the occurrence of periodontal diseases. For example, a study in Japan has found that a *Lactobacillus salivarius* (LS1) may be used to effectively prevent dental caries. Additionally, in Helsinki University of Holland, children at the age of 1-6 who have administered milk added with lactobacilli in a long term for preventing dental caries are studied; and, young people who have administered cheeses added with a special probiotic in a short term for preventing dental caries are also studied. The result shows that the number of *Streptococcus mutans* in saliva is reduced by approximately 20% after 3 weeks. Furthermore, a study in Mexico also shows that continually chewing a chewing gum containing lactobacilli treated by heat sterilization once a week for 16 weeks may improve dental caries and reduce the occurrence of dental caries by approximately 42%.

Additionally, several kinds of *lactobacillus* cultures for inhibiting the formation of the dental plaque are disclosed in U.S. Pat. No. 6,036,952, which include *Enterococcus* spp. 1357, *Lactobacillus acidophilus* V20, and *Lactococcus lactis* 1370. In addition, a product containing *lactobacillus* cultures of ATTC PTA-4965 and PTA-4964 is disclosed in U.S. Pat. No. 6,872,565, which is used for inhibiting dental caries caused by bacteria. The inhibition effect achieved by combining the ATTC PTA-4965 or PTA-4964 and an oral mucin or the dental plaque is used for effectively reducing the number of *Streptococcus mutans*. Alternatively, a method of treating and preventing dental caries, dental plaques, and periodontal diseases with *lactobacillus* cultures CNCM I-1984, CNCM I-1985, CNCM I-1986, CNCM I-1987, or LMG P-18997 is disclosed in U.S. Pat. No. 6,942,849, wherein the *lactobacillus*cultures are genetically modified to enhance the viscosity for a tooth surface film.

Currently, it is found that, *Lactobacillus paracasei* may be used to promote an immunocyte to release a number of interferon, which is helpful for improving allergic diseases. Human immunocyte T lymphocytes are divided into two types according to the secreted different cytokines, wherein there is a dynamic balance between Type I and Type II T lymphocytes, and both of them are influenced by each other, thereby affecting the result of a reaction of the whole immune system to an antigen. If the reaction of Type II T lymphocyte is excessively strong, an allergic symptom occurs to a patient. The allergy may be prevented by increasing the activity of Type I T lymphocyte or inhibiting the activity of Type II T lymphocyte. When the *Lactobacillus paracasei* is used in human bowel, due to the difference of cell walls and cell contents, the *Lactobacillus paracasei* significantly promotes the activity of Type I T lymphocyte and further inhibits the effect of Type II T lymphocyte, and thus preventing allergy.

To sum up, a variety of lactobacilli are now found to have the function of inhibiting dental caries, dental plaques, and periodontal diseases. The *Lactobacillus paracasei* has been used in human bowel in the past to relieve the body allergic symptom after being absorbed by the bowel. However, the efficacy that the *Lactobacillus paracasei* is used in oral cavity to prevent dental diseases has not been found yet.

SUMMARY OF THE INVENTION

The prevent invention provides a *Lactobacillus paracasei*-containing product, which is used for inhibiting dental diseases caused by bacteria, such as dental caries, dental plaques, and periodontal diseases.

The *Lactobacillus paracasei*-containing product disclosed in the prevent invention is used for inhibiting dental diseases caused by bacteria, which comprises a plurality of *Lactobacillus paracasei* for inhibiting the growth of bacteria of dental diseases.

Foods, oral hygiene products or oral treatment medicine containing the *Lactobacillus paracasei* when being administered or applied to a user can inhibit or reduce the number of pathogens of dental caries and periodontal diseases in oral cavity of the user, thereby achieving the efficacy of preventing dental diseases, such as dental caries and periodontal diseases.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given herein below for illustration only, and thus is not limitative of the present invention, and wherein:

FIG. 4A shows a result for inhibiting the growth of pathogens of periodontal disease with an active *Lactobacillus paracasei*; and FIG. 4B shows a result for; inhibiting the growth of pathogens of periodontal disease with a sterilized *Lactobacillus paracasei*.

DETAILED DESCRIPTION OF THE INVENTION

To further understand the objective, structure, feature, and function of the present invention, the present invention is illustrated below in great detail through the embodiments. The above illustration about the summary of the prevent invention and the following illustration about the detailed description of the present invention are intended to demonstrate and explain the principle of the present invention, and provide further explanations for claims of the prevent invention.

I. Screening and Identification of the *Lactobacillus Paracasei*

First of all, a functional *lactobacillus* culture for alleviating dental disease symptoms is screened from the *lactobacillus* cultures existed in human bowel, which is a special *lactobacillus* culture for preventing dental caries screened from *lactobacillus* cultures in a culture collection center via the antimicrobial cycle test with the main pathogens *Streptococcus mutans* and *Streptococcus sobrinus* that cause the formation of dental caries. This functional *lactobacillus* culture is incubated in a culture dish without oxygen at a culture temperature of 37° C. for 16-24 hours. It is found in an experimental analysis that this *lactobacillus* culture is a Gram-positive bacteria, a non-sporing anaerobes, and a non-mobility, which is consistent with the property of the *Lactobacillus paracasei*.

Figure 1:
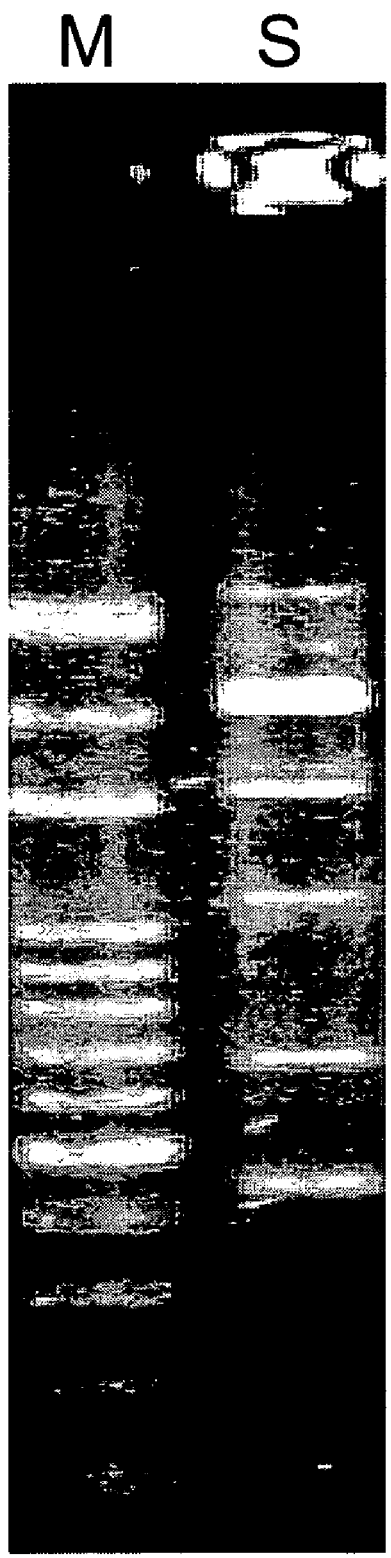
FIG. 1 is a DNA finger map of a *Lactobacillus paracasei*.

To confirm whether the screened *lactobacillus* culture is the *Lactobacillus paracasei*, the assay of random amplified polymorphic DNA-polymerase chain reaction (RAPD-PCR) is carried out for the *lactobacillus* culture. As shown in FIG. 1, the RAPD-PCR technology is used to generate a DNA fingerprint S of the *lactobacillus*culture with an arbitrary primer. After comparison, it is found that the DNA fingerprint S does consistent with the *Lactobacillus paracasei* and it is different with other *lactobacillus* cultures. M in the figure indicates a tagged molecule of molecular weight.

Then, a nucleotide sequencing is carried out for the *lactobacillus* culture with PAF and 536R primers. The sequencing result is compared with a gene database (the website is www.ncbi.nlm.nih.gov), and then, it is confirmed that this *lactobacillus*culture is the *Lactobacillus paracasei*. A part of the nucleotide sequencing result of the *lactobacillus* culture is shown as follows:

```
AACGAGTTCTCGTTGATGATCGGTGCTTGCACCGAGATTCAACATGG
AACGAGTGGCGGACGGGTGAGTAACACGTGGGTAACCTGCCCTTAAGTGG
GGGATAACATTTGGAAACAGATGCTAATACCGCATAGATCCAAGAACCGC
ATGGTTCTTGGCTGAAAGATGGCGTAAGCTATCGCTTTTGGATGGACCCG
CGGCGTATTAGCTAGTTGGTGAGGTAATGGCTCACCAAGGCGATGATACG
TAGCCGAACTGAGAGGTTGATCGGCCACATTGGGACTGAGACACGGCCCA
AACTCCTACGGGAGGCAGCAGTAGGGAATCTTCCACAATGGACGCAAGTC
TGATGGAGCAACGCCGCGTGAGTGAAGAAGGCTTTCGGGTCGTAAAACTC
TGTTGTTGGAGAAGAATGGTCGGCAGAGTAACTGTTGTCGGCGTGACGGT
ATCCAACCAGAAAGCCACGGCTAACTACGTGCCAGCAGCGNGGGTTAATT
AAAA
```

The comparison result of the gene database is shown as follows:

gi|55418407|gb|AY773955.1| *Lactobacillus paracasei* isolate 9C . . .

gi|55418405|gb|AY773953.1| *Lactobacillus paracasei* isolate 3C . . .

gi|55418404|gb|AY773952.1| *Lactobacillus paracasei* isolate 2C . . . .

Finally, the carbohydrate metabolism performance of the *lactobacillus* culture is tested with an API 50 CHL reagent. The API 50 CHL reagent is used for identifying the difference of cultures in genus or species. It is determined by analyzing the result that, the activity of carbohydrate metabolism of the *lactobacillus* culture is the same as that of the *Lactobacillus paracasei* (not shown in data).

The screened special lactobacillus culture for preventing dental diseases is determined to be the *Lactobacillus paracasei* after being identified by the above analysis result.

II. Inhibition Effect of the *Lactobacillus Paracasei* for the Pathogen of Dental Caries 1. Bacteria Test An antimicrobial cycle test for inhibiting the pathogen of dental caries is carried out after being modified according to the method of the National Committee for Clinical Laboratory Standards (NCCLS). A platinum loop of pathogens of dental caries is inoculated in a desired culture medium. The strain is incubated at 37° C. for 18 hours to reach a log-growth phase. The bacteria count is measured with a Smart Spec™ 3000 Spectrophtometer, and the count of pathogens of dental caries is adjusted to $1.5 \times 10^8$ CFU/mL. The *Streptococcus mutans* and *Streptococcus sobrinus* are uniformly applied on the desired culture medium with a thickness of 4 mm, which is stand for 15 minutes, such that the coated bacteria solution is completely adhered on the culture medium. An asepsis filter paper disc with a diameter of 6 mm is used to soak and receive the solution of the *Lactobacillus paracasei*. The asepsis filter paper disc is gently pressed to be completely adhered on the culture medium that is uniformly coated with the *Streptococcus mutans* and *Streptococcus sobrinus*. The size of the antimicrobial cycle is judged and read after incubation at 37° C. for 72 hours.

Figures 2A, 2B:
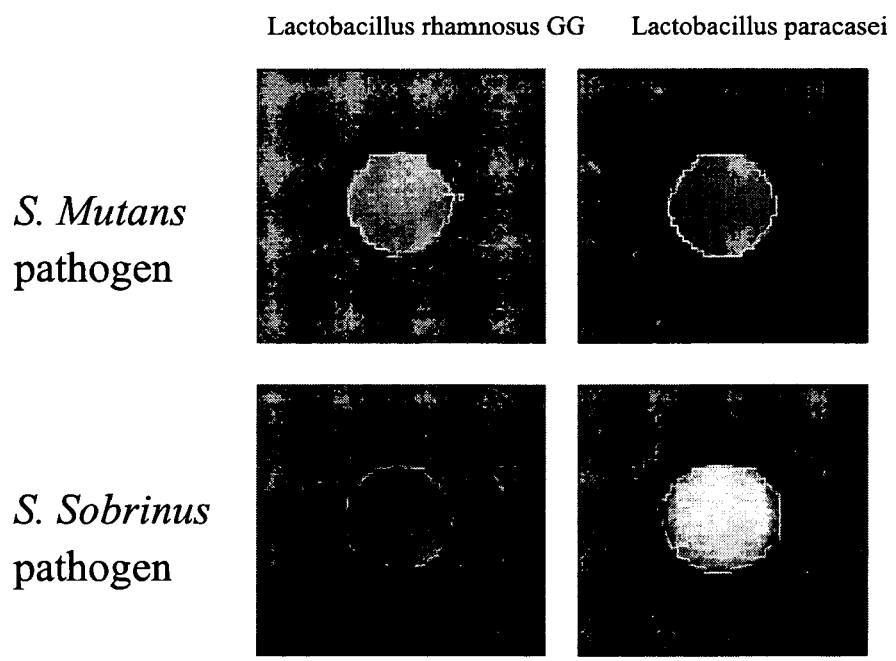
FIGS. 2A and 2B are results of an antimicrobial cycle test for inhibiting the pathogens of dental caries with the *Lactobacillus paracasei*.

Referring to FIGS. 2A and 2B, they are results of the antimicrobial cycle test for inhibiting the pathogens of dental caries. After the *Lactobacillus paracasei* and the pathogens of dental caries were incubated together at 37° C. for 72 hours, the size of the antimicrobial cycle of the main pathogens *Streptococcus mutans* (*S. mutans*) and *Streptococcus sobri-* nus (*S. sobrinus*) that cause dental caries is judged and read. The result of the test shows that, the antimicrobial cycle caused by the *Lactobacillus paracasei* for the two trains of pathogens is larger than that of a *Lactobacillus rhamnosus* GG, i.e., the competitive antagonize effect of the *Lactobacillus paracasei* for the *Streptococcus mutans* and *Streptococcus sobrinus* is more preferable than that of the *Lactobacillus rhamnosus* GG. The *Lactobacillus rhamnosus* GG is a *lactobacillus* culture now widely used in healthy foods for reducing the occurrence of dental caries. Therefore, using the *Lactobacillus paracasei* in oral cavity is helpful for reducing the number of the *Streptococcus mutans*, the occurrence of dental caries, and the occurrence of the periodontal diseases caused by dental caries and bacteria.

2. Animal Test:

Female pregnant Sprague-Dawley (SD) mice are bought from the National Laboratory Animal Center. When infant mice are 18 days old, a 0.2 ml culture solution incubated overnight for the pathogen *S. sobrinus* of dental caries at a log-growth phase is touched with a cotton stick, and then, the culture solution is applied in the oral cavity of female mice for inocuability. A 10% aqueous sucrose solution is available for the female mice without limitation. The step of inocuability is repeated at the second day. The caries bacteria *S. sobrinus* is applied in the oral cavity of the female mice with a sterile cotton stick at the third day of inocuability; and then, it is incubated in a *Mitis Salivarius* culture medium containing 100 µg/ml *Streptomycin*; finally, it is inspected whether the inocuability is successful.

The SD infant mice are ablactated on the 20$^{th}$ day, and then, they are divided into groups. A 0.2 ml culture solution incubated overnight for the pathogen *S. sobrinus* of dental caries at a log-growth phase is touched with a cotton stick, and then, the culture solution is applied in the oral cavity of SD infant mice for inocuability. A 10% aqueous sucrose solution is available for the SD infant mice without limitation. The step of inocuability is repeated at the second day. The caries bacteria *S. sobrinus* is applied in the oral cavity of the SD infant mice with a sterile cotton stick at the third day of inocuability; and then, it is incubated in a *Mitis Salivarius* culture medium containing 100 µg/ml *Streptomycin*; finally, it is inspected whether the inocuability is successful.

The aqueous sucrose solution is available for the SD infant mice without limitation during the period from the 23$^{rd}$ day since the mice were born to the completion of the test. Body weights are measured before the efficacy test, and the body weights are measured once a week during the test. The SD infant mice are sacrificed after 5 weeks for observing the degree of dental caries.

Figure 3A:
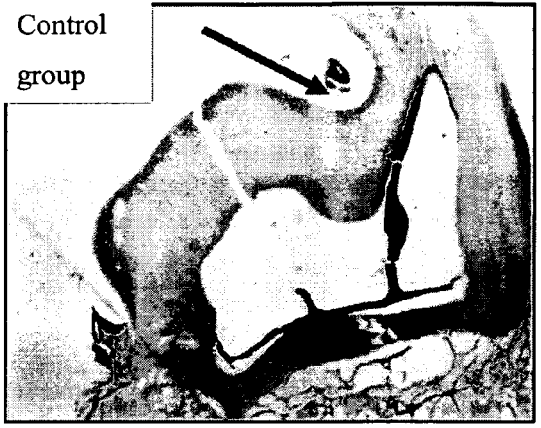
FIG. 3A is a result of an animal test in a control group.
Figure 3B:
FIG. 3B is a result of an animal test after inoculation of a pathogen *S. sobrinus*.
Figure 3C:
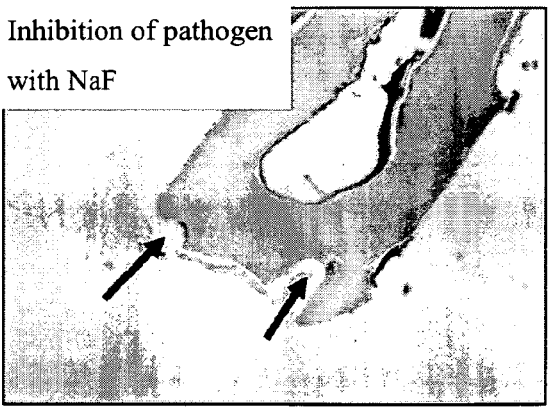
FIG. 3C is a result of an animal test for inhibiting the pathogen with a sodium fluoride after inoculation of the pathogen *S. sobrinus*.
Figure 3D:
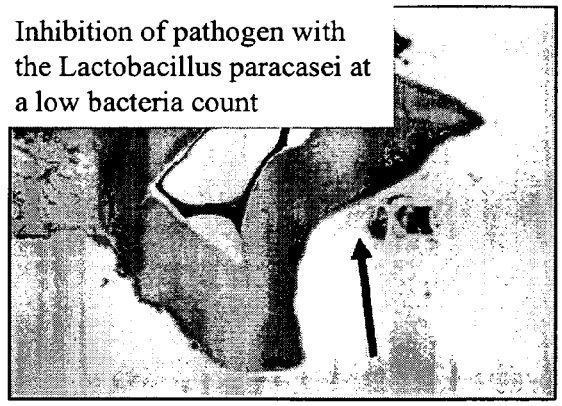
FIG. 3D is a result of an animal test for inhibiting the pathogen with the *Lactobacillus paracasei* at a low bacteria count after inoculation of the pathogen *S. sobrinus*.
Figure 3E:
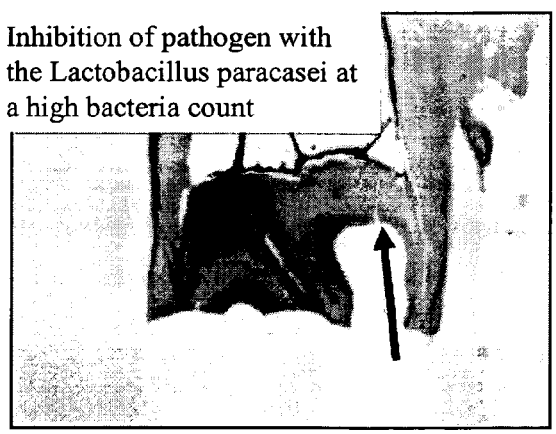
FIG. 3E is a result of an animal test for inhibiting the pathogen with the *Lactobacillus paracasei* at a high bacteria count after inoculation of the pathogen *S. sobrinus*.

Referring to FIGS. 3A-3E, they show results of the animal test for inhibiting the pathogens of dental caries. FIG. 3A is a test result of a bank group. The pathogens of dental caries are not incubated, and the aqueous sucrose solution added with the *Lactobacillus paracasei* is not available throughout the test. FIG. 3B is a test result of the inoculation of a pathogen *S. sobrinus*. FIG. 3C is a test result for using an aqueous sucrose solution containing 0.022% NaF after inoculation of the pathogen *S. sobrinus*. FIG. 3D is a test result for using an aqueous sucrose solution containing 5×10$^9$ CFU/ml *Lactobacillus paracasei* after inoculation of the pathogen *S. sobrinus*. FIG. 3E is a test result for using an aqueous sucrose solution containing 5×10$^{11}$ CFU/ml *Lactobacillus paracasei* after inoculation of the pathogen *S. sobrinus*.

The test conditions in FIG. 3C include that the aqueous sucrose solution containing 0.022% NaF is available for the mice from the 23$^{rd}$ day after the inoculation for the pathogen *S. sobrinus* of dental caries is successful; the pH value of the aqueous solution is 7; the concentration of Fluoride ion is 100 ppm. The test conditions in FIGS. 3D and 3E include that the *Lactobacillus paracasei* at the bacteria count of 5×10$^9$ CFU/ml and 5×10$^{11}$ CFU/ml are respectively fed to the mice at 23 days after the inoculation for the pathogen *S. sobrinus* of dental caries is successful. Each SD mouse is fed with 0.05 ml on left and right cheek respectively once a day, which is totally fed with 0.1 ml of the *Lactobacillus paracasei* each day.

The test for the above test groups lasts for 5 weeks. The tooth of the mice is sliced to observe the depth caused by dental caries after the test is completed. The result of FIG. 3B indicates that, after the inoculation of the *S. sobrinus* culture solution, the aqueous sucrose solution is available without limitation for 5 weeks, so that the depth of dental caries is the most serious even to invade the part of the tooth marrow as indicated by the black arrows in FIG. 3B. But only low dental caries were formed, as indicated by the black arrows, when adding NaF (as shown in FIG. 3C) or the *Lactobacillus paracasei* (as shown in FIGS. 3D and 3E) to the aqueous sucrose solution, and the depth of the low dental caries is similar to that caused by dental caries in the control group (as shown in FIG. 3A). This test shows that, the efficacies in preventing the formation of dental caries are equivalent when administering an aqueous sucrose solution containing the *Lactobacillus paracasei* or added with NaF.

III. Inhibition Effect of the *Lactobacillus Paracasei* for the Pathogens of Periodontal Disease The pathogens of periodontal disease selected in this test include *Porphyromonas gingivalis, Prevotella intermedia, Centipeda periodontii*, and a clinic sample of the periodontal disease bacteria obtained from the cheek tooth of a patient on periodontal disease. The pathogens of periodontal disease and the *Lactobacillus paracasei* are shaking-incubated together. After being inoculated for 0, 1, 2, 4, 6, and 12 hours, 5 µl culture solution is taken from the culture solution with 10-fold and 100-fold serial dilution, and then applied on the BBAP culture medium. They are placed in an anaerobic incubator at 37° C. for standing and incubating for 48-96 hours. After colonies have been formed, a colony counter is used to calculate the obtained colonies. It is determined whether there is an inhibition effect of the active *Lactobacillus paracasei* and the sterilized *Lactobacillus paracasei* (dead *Lactobacillus paracasei*) for the pathogens of periodontal disease.

Referring to FIG. 4A, it shows a result for inhibiting the growth of pathogens of periodontal disease with an active *Lactobacillus paracasei*. As shown in the table that, the active *Lactobacillus paracasei* indeed causes the phenomenon of inhibiting the growth of pathogens of periodontal disease, and when the pathogens *Porphyromonas gingivalis* and *Centipeda periodontii* are respectively combined and reacted with the active *Lactobacillus paracasei* for 1 hour, over 80% inhibiting ratio is achieved, and when the above two pathogens are reacted with the active *Lactobacillus paracasei* for 2 hours, the two pathogens (an inhibiting ratio of 100%) will be completed eliminated. As for the inhibition effect for *Prevotella intermedia*, when it is combined and reacted with the active *Lactobacillus paracasei* for 1 hour, an inhibiting ratio of about 70% is achieved, and a maximum inhibiting ratio (an inhibiting ratio of 80-90%) occurs after it is combined and reacted with the active *Lactobacillus paracasei* for 6 hours. The only tested clinic sample is the specimen of the dental plaques under the gingiva. Since the clinic sample is a combined flora, the symbiosis may enhance the pathogens' resistance, and an inhibiting ratio of about 50% is achieved after being combined and reacted with the active *Lactobacillus paracasei* for 1 hour, and the inhibiting ratio is increased to about 70% after 2 hours, and the inhibiting ratio is changed slightly as the prolonging of the combining and reacting duration.

Referring to FIG. 4B, it shows a result for inhibiting the growth of pathogens of periodontal disease with a sterilized *Lactobacillus paracasei*. The inhibition effect of the essentially sterilized *Lactobacillus paracasei* for the growth of pathogens of periodontal disease is lower than that of the active *Lactobacillus paracasei*. As for the pathogens of periodontal disease, an inhibiting ratio of 50-70% is achieved after combining and reacting the dead *Lactobacillus paracasei* with the pathogens of periodontal disease for 1 hour. As for the pathogens *Porphyromonas gingivalis* and *Centipeda periodontii* of periodontal disease, an inhibiting ratio close to 80% is achieved after combining and reacting the dead *Lactobacillus paracasei* with the pathogens *Porphyromonas gingivalis* and *Centipeda periodontii* of periodontal disease for 4 hours. As for the *Prevotella intermedia*, an inhibiting ratio close to 60% is achieved after combining and reacting the dead *Lactobacillus paracasei* with the *Prevotella intermedia* for 4 hours. As for the clinic sample, an inhibiting ratio of less than 50% is achieved after combining and reacting the clinic sample with the *Prevotella intermedia* for 1 hour. The maximum inhibiting ratio occurs after the combining process has lasted for 12 hours (inhibiting ratio of about 60%).

The result of this test shows that, although the inhibition effect of the sterilized *Lactobacillus paracasei* for pathogens of periodontal disease is weaker than that of the active *Lactobacillus paracasei*, the sterilized *Lactobacillus paracasei* still has the inhibition effect.

IV. Conclusion

The high occurrence of dental caries is determined in clinic according to whether the bacteria count of the pathogen *Streptococcus mutans* is higher than $10^6$ CFU/ml. Therefore, the special *lactobacillus* strain for preventing dental caries is screened by the antimicrobial cycle test of the *lactobacillus* cultures for the pathogens *Streptococcus mutans* and *Streptococcus sobrinus* of dental caries, which is aimed at inhibiting the growth of the *Streptococcus mutans* by using the lactobacilli, and thereby reducing the occurrence of dental caries. It is confirmed via a series of inhibition tests that, the *Lactobacillus paracasei* has the efficacy of inhibiting dental caries and pathogens of periodontal disease.

The widely known health care function of the *Lactobacillus paracasei* lies in enhancing immunity and preventing allergy. However, when the products containing the *Lactobacillus paracasei* produced according to the prevent invention, such as food, oral care products or oral treatment medicine, are administered or used by a user, no matter the products contain the active *Lactobacillus paracasei* or the dead *Lactobacillus paracasei*, they inhibit the pathogens of dental caries and periodontal disease in oral cavity of the user with the *Lactobacillus paracasei*, so as to achieve the efficacy of treating and preventing dental caries and periodontal disease. The functional *lactobacillus*—*Lactobacillus paracasei* suitable for human body is used for preventing the dental caries and alleviating the periodontal disease symptoms. When the products containing the *Lactobacillus paracasei* are used in oral cavity for treating dental diseases, they do not cause the non-adaptation of human body, and also do not have the risk as typical noxious fluorides for curing the dental caries.

A deposit designation of a culture of the *Lactobacillus paracasei* GMNL-33 in the present invention was deposited with the Food Industry Research and Development Institute, Bioresource Collection and Research Center located at 331 Shih-Pin Road, Hsinchu, Taiwan on Mar. 22, 2006 and has BCRC910314 as an internal Patent Deposit Designation and GMNL-33 as a Depositor Identification Reference. *Lactobacillus paracasei* GMNL-33 was also deposited in the China Center for Type Culture Collection (CCTCC) located at Wuhan University, Wuhan 430072 P.R. China with Accession No. CCTCC M 206133 on Nov. 27, 2006 under the Budapest Treaty. The food containing the *Lactobacillus paracasei* of the present invention may be a liquid food, for example, drink products added with the *Lactobacillus paracasei* such as juice, milk, and tea. The food may also be a solid food such as confection, troche, biscuit, chocolate, and cheese added with the *Lactobacillus paracasei*. In addition, the food may also a gel food, such as yoghourt, jelly, pudding, and gum added with the *Lactobacillus paracasei*. This type of food is suitable for children to prevent dental caries. The product containing the *Lactobacillus paracasei* in the present invention also includes an oral hygiene product, such as toothpastes and gargles added with the *Lactobacillus paracasei*, and the *Lactobacillus paracasei* is used to replace the typical fluoride for inhibiting the pathogens of dental disease and thereby provide a safe and effective protection for teeth. In addition, the product containing the *Lactobacillus paracasei* also includes an oral treatment medicine, such as ointments and troches added with the *Lactobacillus paracasei*. The ointments are applied on the surface of teeth or the troches are used in oral cavity in a long term, such that the time duration for the *Lactobacillus paracasei* to be reacted with the pathogens is prolonged. thus, the growth of the pathogens is more effectively inhibited.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A *Lactobacillus paracasei*-containing product for inhibiting dental diseases caused by bacteria, comprising a biologically pure *Lactobacillus paracasei* strain CCTCC M 206133.

2. The *Lactobacillus paracasei*-containing product as claimed in claim 1, wherein the product is a liquid food.

3. The *Lactobacillus paracasei*-containing product as claimed in claim 2, wherein the liquid food includes a juice, milk, or tea.

4. The *Lactobacillus paracasei*-containing product as claimed in claim 1, wherein the product is a solid food.

5. The *Lactobacillus paracasei*-containing product as claimed in claim 4, wherein the solid food includes a confection, troche, biscuit, chocolate, or cheese.

6. The *Lactobacillus paracasei*-containing product as claimed in claim 1, wherein the product is a gel food.

7. The *Lactobacillus paracasei*-containing product as claimed in claim 6, wherein the gel food includes a yoghourt, jelly, pudding, or gum.

8. The *Lactobacillus paracasei*-containing product as claimed in claim 1, wherein the product is an oral hygiene product.

9. The *Lactobacillus paracasei*-containing product as claimed in claim 8, wherein the oral hygiene product is toothpaste.

10. The *Lactobacillus paracasei*-containing product as claimed in claim 8, wherein the oral hygiene product is a gargle.

11. The *Lactobacillus paracasei*-containing product as claimed in claim 1, wherein the product is an oral treatment medicine.

12. The *Lactobacillus paracasei*-containing product as claimed in claim 11, wherein the oral treatment medicine is an ointment.

13. The *Lactobacillus paracasei*-containing product as claimed in claim 11, wherein the oral treatment medicine is a troche.

* * * * *

SEQUENCE LISTING

```
<160> NUMBER OF SEQ ID NOS: 1

<210> SEQ ID NO 1
<211> LENGTH: 501
<212> TYPE: DNA
<213> ORGANISM: Lactobacillus paracasei
<220> FEATURE:
<221> NAME/KEY: misc_feature
<222> LOCATION: (488)..(488)
<223> OTHER INFORMATION: n is a, c, g, or t
```

-continued

```
<400> SEQUENCE: 1
aacgagttct cgttgatgat cggtgcttgc accgagattc aacatggaac gagtggcgga        60
cgggtgagta acacgtgggt aacctgccct taagtggggg ataacatttg gaaacagatg       120
ctaataccgc atagatccaa gaaccgcatg gttcttggct gaaagatggc gtaagctatc       180
gcttttggat ggacccgcgg cgtattagct agttggtgag gtaatggctc accaaggcga       240
tgatacgtag ccgaactgag aggttgatcg gccacattgg gactgagaca cggcccaaac       300
tcctacggga ggcagcagta gggaatcttc cacaatggac gcaagtctga tggagcaacg       360
ccgcgtgagt gaagaaggct ttcgggtcgt aaaactctgt tgttggagaa gaatggtcgg       420
cagagtaact gttgtcggcg tgacggtatc caaccagaaa gccacggcta actacgtgcc       480
agcagcgngg gttaattaaa a                                                 501
```